US009724264B2

(12) United States Patent
Cai

(10) Patent No.: US 9,724,264 B2
(45) Date of Patent: Aug. 8, 2017

(54) CONTROL SYSTEM, CONTROL METHOD, REMOTE INTERACTIVE CONTROL SYSTEM AND REMOTER INTERACTIVE CONTROL METHOD FOR SEXUAL STIMULATION DEVICE

(71) Applicant: Danzhi Cai, Shenzhen (CN)

(72) Inventor: Danzhi Cai, Shenzhen (CN)

(73) Assignee: Danzhi Cai, Shenzhen (CN)

( * ) Notice: Subject to any disclaimer, the term of this patent is extended or adjusted under 35 U.S.C. 154(b) by 404 days.

(21) Appl. No.: 14/606,023

(22) Filed: Jan. 27, 2015

(65) Prior Publication Data

US 2016/0213556 A1 Jul. 28, 2016

(51) Int. Cl.

| | |
|---|---|
| ***A61F 5/00*** | (2006.01) |
| ***A61H 19/00*** | (2006.01) |
| ***A61H 23/02*** | (2006.01) |

(52) U.S. Cl.

CPC ............. *A61H 19/34* (2013.01); *A61H 19/44* (2013.01); *A61H 23/0263* (2013.01); *A61H 2201/5005* (2013.01); *A61H 2201/5007* (2013.01); *A61H 2201/5043* (2013.01); *A61H 2201/5058* (2013.01); *A61H 2201/5061* (2013.01); *A61H 2201/5097* (2013.01)

(58) Field of Classification Search

CPC ........ A61H 19/00; A61H 19/34; A61H 19/40; A61H 19/44; A61H 23/0263
USPC ........................................ 600/38–41; 601/46
See application file for complete search history.

(56) References Cited

U.S. PATENT DOCUMENTS

2003/0069470 A1* 4/2003 Lee ........................ A61H 19/44 600/38
2014/0336452 A1* 11/2014 Shahoian et al. ...... A61H 19/30 600/38

* cited by examiner

*Primary Examiner* — John Lacyk
(74) *Attorney, Agent, or Firm* — Steven Reiss

(57) ABSTRACT

A control method is provided. The control method is applied to a sexual stimulation device including a vibration unit. The control method comprises the steps as follows. A communication connection is established between the sexual stimulation device and an intelligent terminal. A pressure of the sexual stimulation device and a moving speed of the sexual stimulation device are detected in real time. The detected pressure and the detected speed are obtained. A detect signal containing the detected pressure and the detected speed is generated. The detect signal is submitted to the intelligent terminal. A control signal is generated by the intelligent terminal according to the detect signal and further transmitted to the sexual stimulation device. The sexual stimulation device is controlled to vibrate according to the control signal.

20 Claims, 12 Drawing Sheets

CONTROL SYSTEM, CONTROL METHOD, REMOTE INTERACTIVE CONTROL SYSTEM AND REMOTER INTERACTIVE CONTROL METHOD FOR SEXUAL STIMULATION DEVICE

FIELD

The subject matter herein generally relates to control systems, control methods, remote interactive control systems and remoter interactive control methods for sexual stimulation devices.

BACKGROUND

Many sexual stimulation devices are presently available for use by men or women who with or without a partner being involved. These devices can be strictly manual or include a vibration mechanism, and may be used either internally to stimulate the vagina and G-spot, or externally to stimulate the clitoris, and may also provide mutual stimulation depending upon their design.

BRIEF DESCRIPTION OF THE DRAWINGS

Many aspects of the present disclosure are better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

Figure 1:
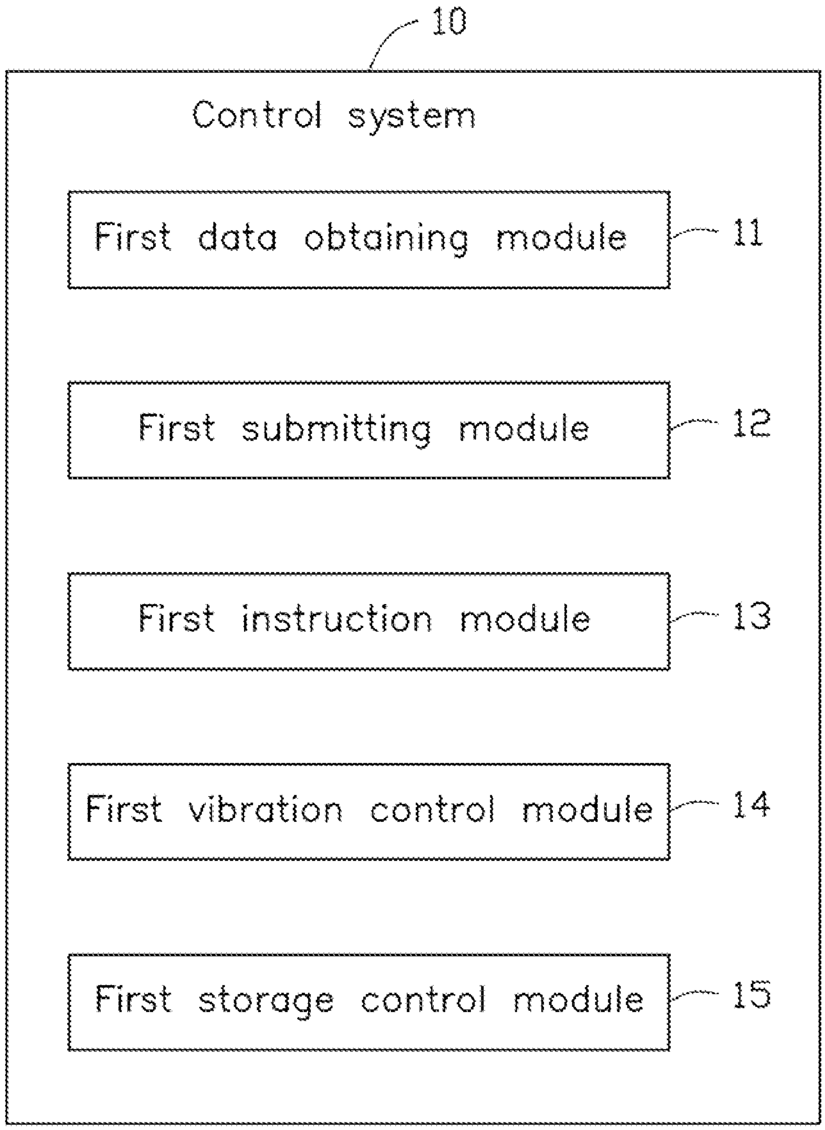
FIG. 1 is a block diagram of an embodiment of a control system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. Also, the description is not to be considered as limiting the scope of the embodiments described herein. The drawings are not necessarily to scale and the proportions of certain parts may be exaggerated to better illustrate details and features of the present disclosure.

A definition that applies throughout this disclosure will now be presented.

The term "comprising," when utilized, means "including, but not necessarily limited to"; it specifically indicates open-ended inclusion or membership in the so-described combination, group, series and the like.

Figure 2:
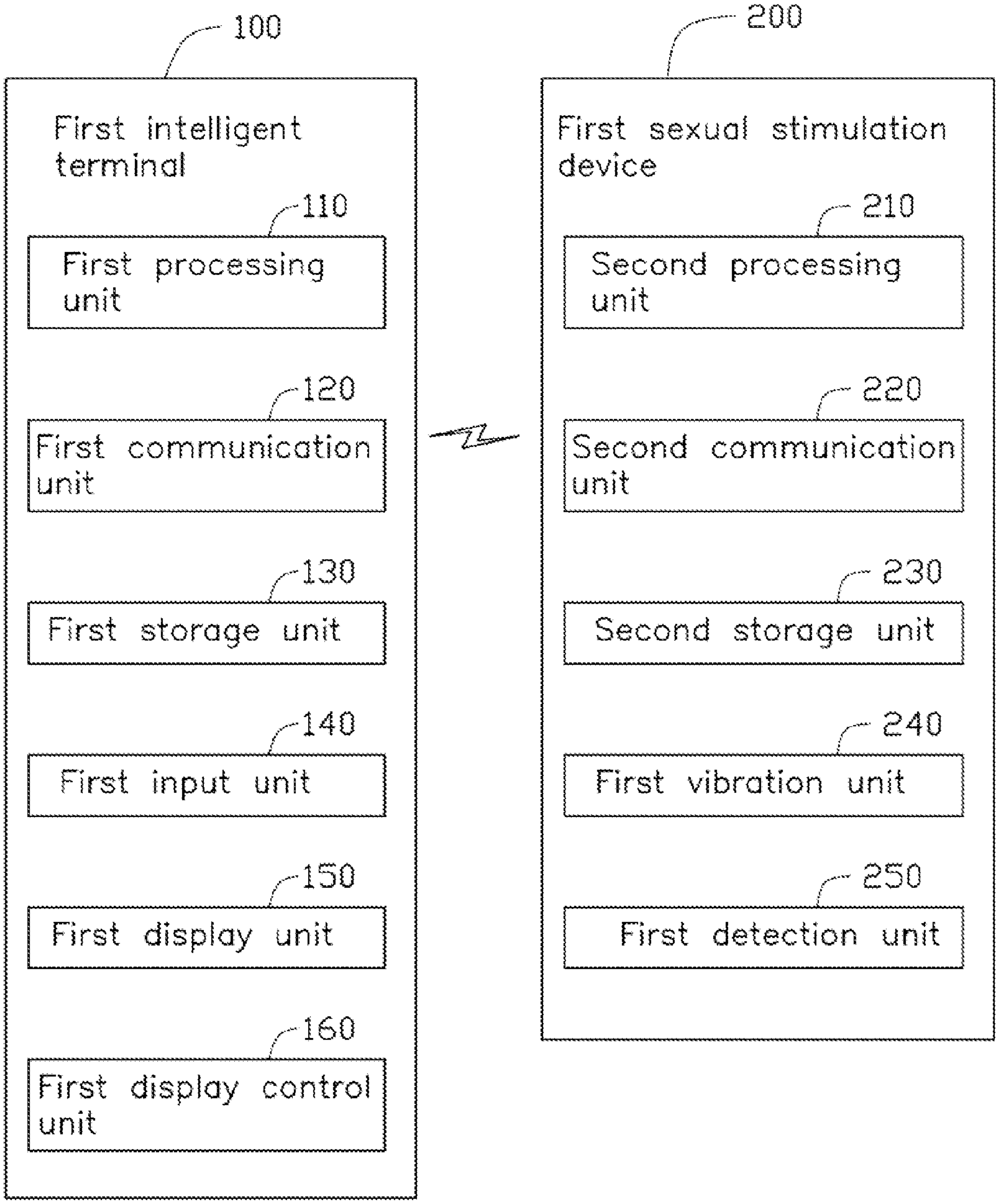
FIG. 2 is a block diagram of an embodiment of an operating environment of a control method.
Figure 11:
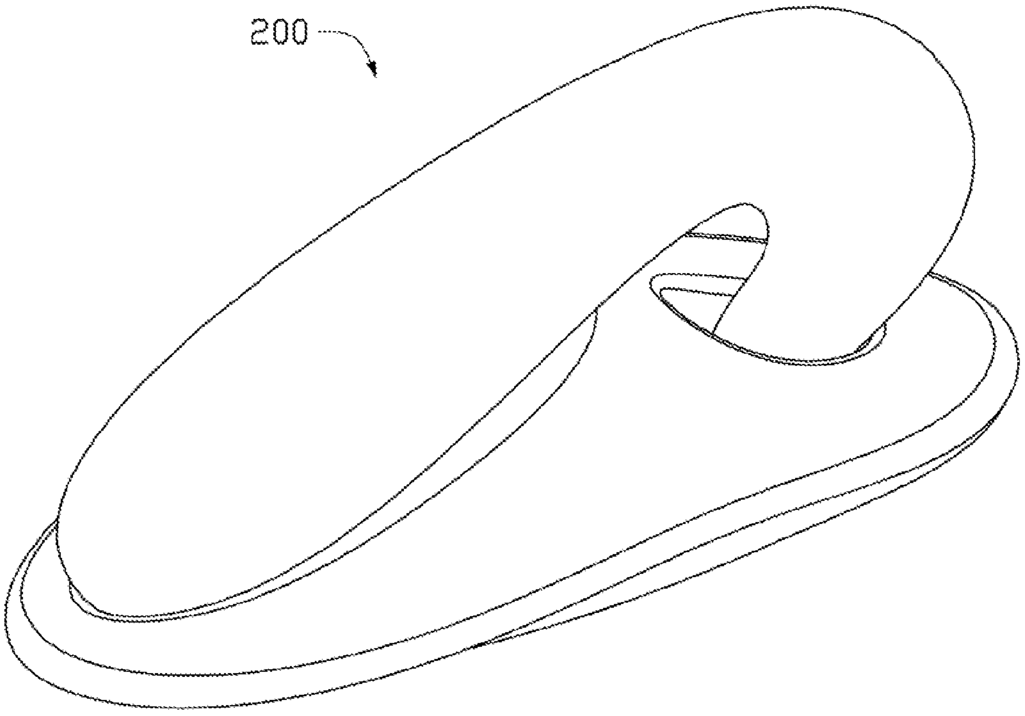
FIG. 11 is an isometric view of an embodiment of a female sexual stimulation device.

Referring to FIGS. 1 and 2, a control system 10 is illustrated. The control system 10 is run in a first intelligent terminal 100 and a first sexual stimulation device 200 as shown in FIG. 2. The first sexual stimulation device 200 can be a female sexual stimulation device, as shown in FIG. 11, for female to use.

The first intelligent terminal 100 can be a mobile phone, a computer includes, but not limited to, a portable computer, a tablet computer, a desktop computer. The first intelligent terminal 100 can include a first processing unit 110, a first communication unit 120, a first storage unit 130, a first input unit 140, a first display unit 150 and a first display control unit 160.

The first display control unit 160 can be used to control the first display unit 150 to display contents.

The first sexual stimulation device 200 can include a second processing unit 210, a second communication unit 220, a second storage unit 230, a first vibration unit 240 and a first detection unit 250.

The second communication unit 220 can be used to connect to the first communication unit 120 of the first intelligent terminal 100.

The first storage unit 130 and the second storage unit 230 are both used for storing a number of vibration modes, a number of vibration strength and a mapping relationship between the number of vibration modes and the number of vibration strength.

The first detection unit 250 can be used to detect a pressure of the first sexual stimulation device 200 and/or a moving speed of the first sexual stimulation device 200 in real time.

The control system 10 can include a first data obtaining module 11, a first submitting module 12, a first instruction module 13, a first vibration control module 14 and a first storage control module 15. In the embodiment, the first instruction module 11 and the first storage control module 15 can be a collection of software instructions stored in the first storage unit 130 of the first intelligent terminal 100 and executed by the first processing unit 110 of the first intelligent terminal 100. The first data obtaining module 11, the first submitting module 12 and the first vibration control module 14 can be a collection of software instructions stored in the second storage unit 230 of the first sexual stimulation device 200 and executed by the second processing unit 210 of the first sexual stimulation device 200. The modules of the control system 10 also can include functionality represented as hardware or integrated circuits, or as software and hardware combinations, such as a special-purpose processor or a general-purpose processor with special-purpose firmware.

In other embodiment, the all of modules of the control system 10 can be stored in the first storage unit 130 of the first intelligent terminal 100 and executed by the first processing unit 110 of the first intelligent terminal 100, or can be stored in the second storage unit 230 of the first sexual stimulation device 200 and executed by the second processing unit 210 of the first sexual stimulation device 200.

In one embodiment, the first processing unit 110 and the second processing unit 210 can be a central processing unit, a digital signal processor, or a single chip, for example. In one embodiment, the first storage unit 130 and the second storage unit 230 can be an internal storage system, such as a flash memory, a random access memory (RAM) for temporary storage of information, and/or a read-only memory (ROM) for permanent storage of information. The first storage unit 130 and the second storage unit 230 can also be a storage system, such as a hard disk, a storage card, or a data storage medium. The first storage unit 130 and the second storage unit 230 can include volatile and/or non-volatile storage devices. In at least one embodiment, the first storage unit 130 and the second storage unit 230 can include two or more storage devices such that one storage device is a memory and the other storage device is a hard drive. Additionally, the first storage unit 130 and the second storage unit 230 can be respectively located either entirely or partially external relative to the first intelligent terminal 100 and the first sexual stimulation device 200.

The first data obtaining module 11 can be used to obtain the detected pressure and the detected speed detected by the first detection unit 250 and further generate a first detect signal containing the detected pressure and the detected speed.

The first submitting module 12 is used to control the second communication unit 220 of the first sexual stimulation device 200 to submit the first detect signal to the first intelligent terminal 100.

The first display control unit 160 of the first intelligent terminal 100 can be used to control the first display unit 150 to display the detected pressure and the detected speed by dynamic graphics according to the first detect signal and when the detected pressure and the detected speed are displayed by the first display unit 150, the user can read the detected pressure and the detected speed and select a suitable vibration mode and/or a suitable vibration strength according to the detected pressure and the detected speed.

The first instruction module 13 can be used to generate a first control signal containing a vibration mode and/or a vibration strength in response to a user's input operation applied on the first input unit 140 and further control the first communication unit 120 to transmit the first control signal to the first sexual stimulation device 200.

The first vibration control module 14 can be used to control the first vibration unit 240 of the first sexual stimulation device 200 to vibrate according to the first control signal.

The first control signal can contain control information and the control information can be stored in the first storage unit 130 if the user selects to store the control information. In detail, the first storage control module 15 is used to pop a first dialog box containing a "yes" option and a "no" option to ask the user whether to store the control information in response to the first control signal and further control the first storage unit 130 to store the control information contained in the first control signal in response to the user's input operation of selecting the "yes" option applied on the first input unit 140 or not to store the control information contained in the first control signal in response to the user's input operation of selecting the "no" option applied on the first input unit 140.

Figure 3:
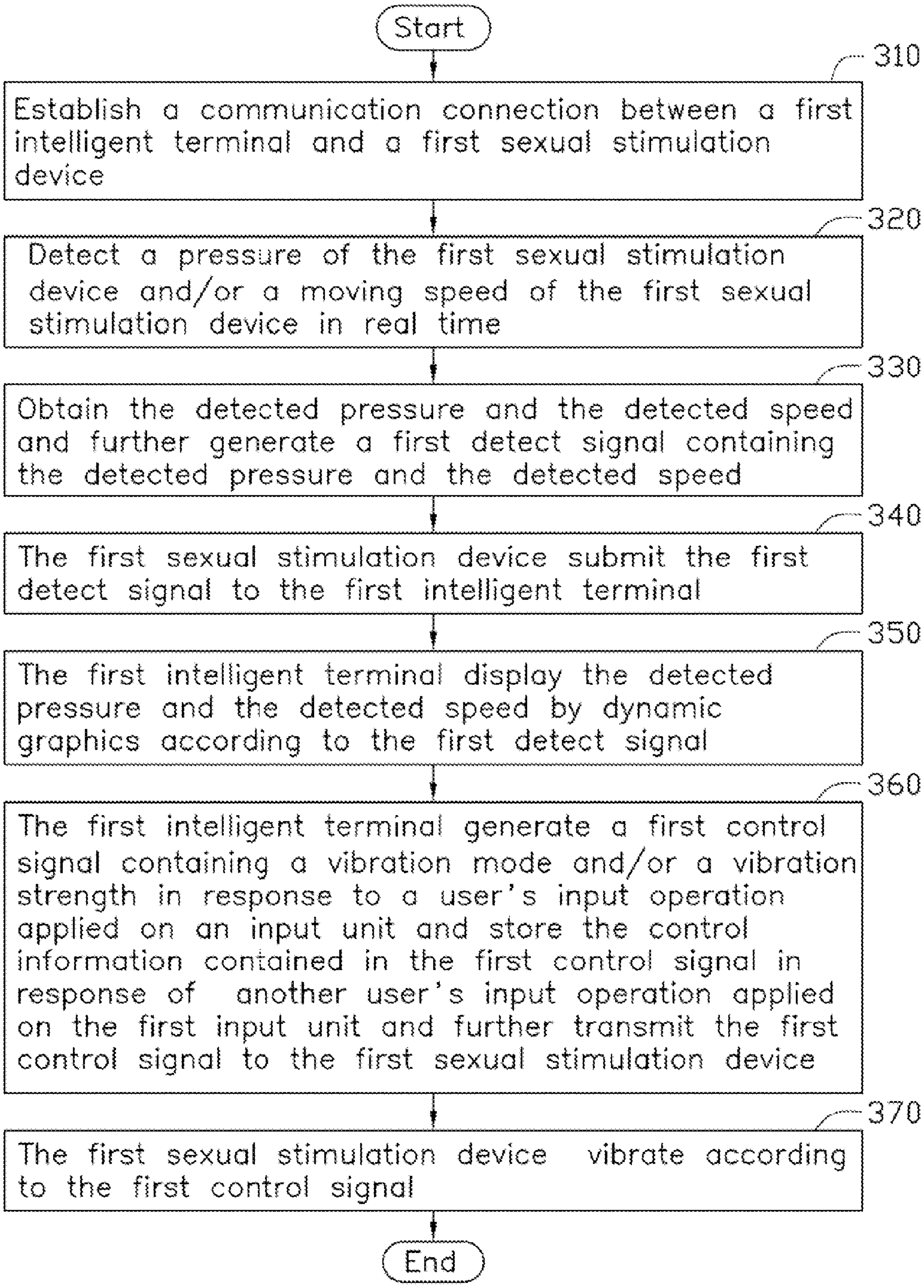
FIG. 3 is a flowchart diagram of an embodiment of a control method.

FIG. 3 illustrates a flowchart of an embodiment of a control method for controlling the first sexual stimulation device 200. The method is provided by way of example, as there are a variety of ways to carry out the method. The method described below can be carried out using the configurations illustrated in FIG. 1, for example, and various elements of these figures are referenced in explaining the example method. Each block shown in FIG. 3 represents one or more processes, methods, or subroutines carried out in the example method. Additionally, the illustrated order of blocks is by example only and the order of the blocks can be changed. The example method can begin at block 310.

At block 310, a first communication unit of the first intelligent terminal and a second communication unit of the first sexual stimulation device establish a communication connection between the first intelligent terminal and the first sexual stimulation device.

At block 320, a first detection unit of the first sexual stimulation device detects a pressure of the first sexual stimulation device and/or a moving speed of the first sexual stimulation device in real time.

At block 330, a first data obtaining module obtains the detected pressure and the detected speed and further generates a first detect signal containing the detected pressure and the detected speed.

At block 340, a first submitting module controls the second communication unit of the first sexual stimulation device to submit the first detect signal to the first intelligent terminal.

At block 350, a first display control unit of the first intelligent terminal controls a first display unit to display the detected pressure and the detected speed by dynamic graphics according to the first detect signal.

At block 360, a first instruction module generates a first control signal containing a vibration mode and/or a vibration strength in response to a user's input operation applied on an input unit and a first storage control module controls a first storage unit to store control information contained in the first control signal in response to a user's input operation of selecting a "yes" option applied on the first input unit and further control the first communication unit of the first intelligent terminal to transmit the first control signal to the first sexual stimulation device.

At block 370, a first vibration control module controls a first vibration unit of the first sexual stimulation device to vibrate according to the first control signal.

Figure 4:
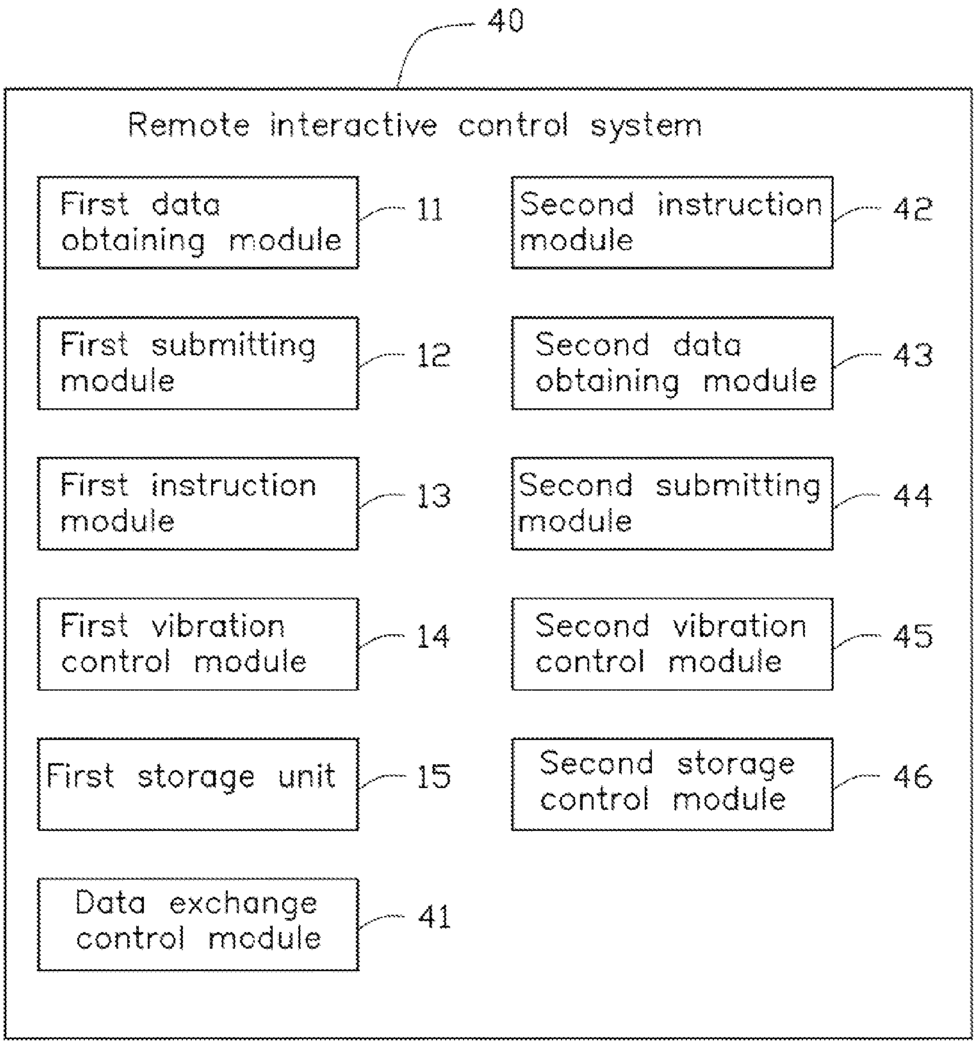
FIG. 4 is a block diagram of an embodiment of a remote interactive control system.
Figure 5:
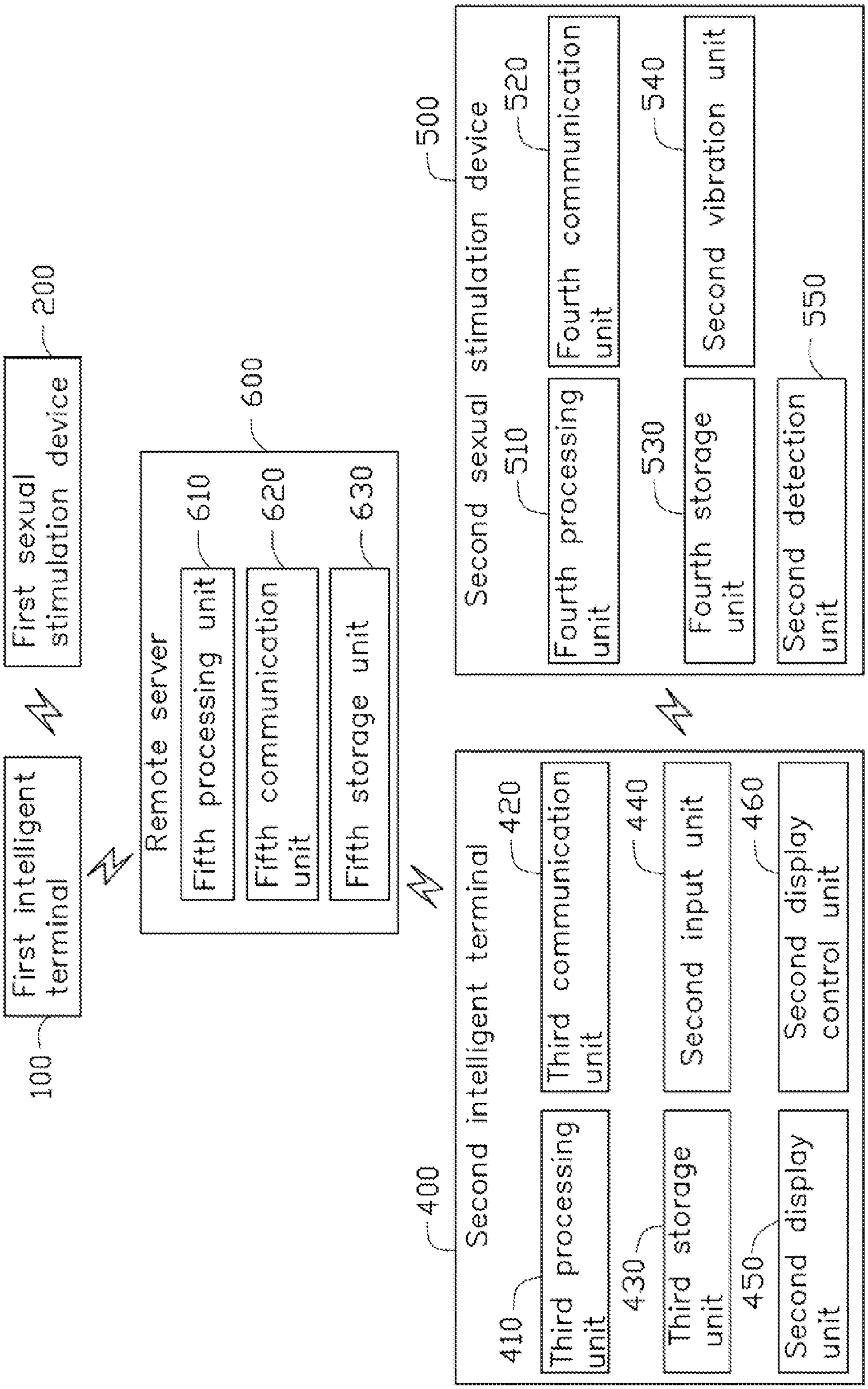
FIG. 5 is a block diagram of an embodiment of an operating environment of a remote interactive control system.

Referring to FIG. 4 and FIG. 5, a remote interactive control system 40 is illustrated. The remote interactive control system 40 is run in at least one first intelligent terminal 100, at least one first sexual stimulation device 200 wirelessly connected to the first intelligent terminal 100, at least one second intelligent terminal 400, at least one second sexual stimulation device 500 wirelessly connected to the second intelligent terminal 400 and a remote server 600, as shown in FIG. 5.

The second intelligent terminal 400 is similar to the first intelligent terminal 100 as shown in FIG. 2. The second intelligent terminal 400 can be a mobile phone, a computer includes, but not limited to, a portable computer, a tablet computer, a desktop computer. The second intelligent terminal 400 can include a third processing unit 410, a third communication unit 420, a third storage unit 430, a second input unit 440, a second display unit 450 and a second display control unit 460.

The second display control unit 460 can be used to control the second display unit 450 to display contents.

Figure 12:
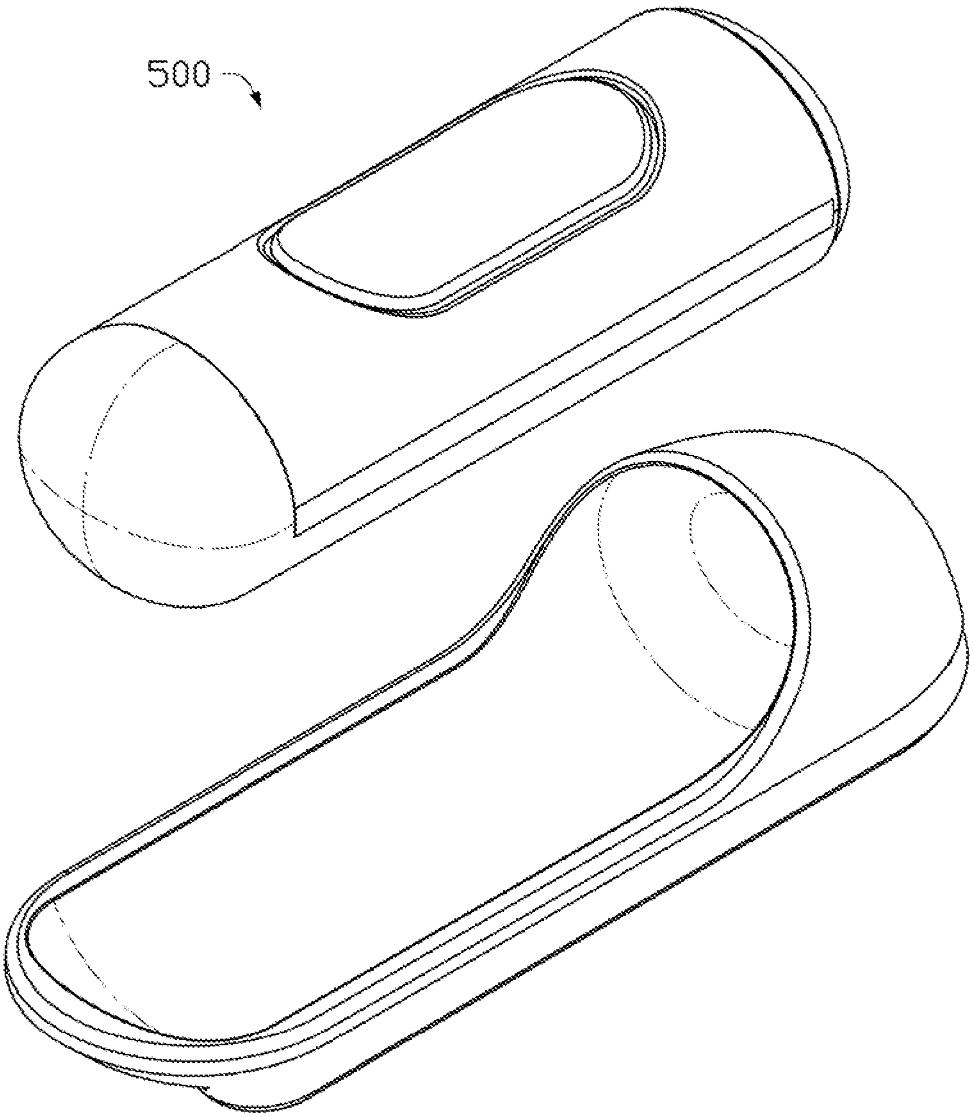
FIG. 12 is an isometric view of an embodiment of a male sexual stimulation device.

The second sexual stimulation device 500 can be a male sexual stimulation device, as shown in FIG. 12, for male to use.

The second sexual stimulation device 500 can include a fourth processing unit 510, a fourth communication unit

520, a fourth storage unit 530, a second vibration unit 540 and a second detection unit 550.

The fourth communication unit 520 can be used to connect to the third communication unit 420 of the second intelligent terminal 400.

The third storage unit 430 and the fourth storage unit 530 can be both used for storing a number of vibration modes, a number of vibration strength and a mapping relationship between the number of vibration modes and the number of vibration strength.

The second detection unit 550 can be used to detect a pressure of the second sexual stimulation device 500 and a moving speed of the second sexual stimulation device 500 in real time.

The remote server 600 can include a fifth processing unit 610, a fifth communication unit 620 and a fifth storage unit 630.

The fifth communication unit 620 can be used to connect to the first communication unit 120 of the first intelligent terminal 100 and/or the third communication unit 420 of the second intelligent terminal 400.

The remote interactive control system 40 can include all the modules of the control system 10. The remote interactive control system 40 can further include a data exchange control module 41, a second instruction module 42, a second data obtaining module 43, a second submitting module 44, a second vibration control module 45 and a second storage control module 46. In the embodiment, the data exchange control module 41 can be a collection of software instructions stored in the fifth storage unit 530 of the remote server 500 and executed by the fifth processing unit 510 of the remote server 500. The second instruction module 42 and the second storage control unit 46 can be a collection of software instructions stored in the third storage unit 430 of the second intelligent terminal 400 and executed by the third processing unit 410 of the second intelligent terminal 400. The second data obtaining module 43, the second submitting module 44 and the second vibration control module 45 can be a collection of software instructions stored in the fourth storage unit 530 of the second sexual stimulation device 500 and executed by the fourth processing unit 510 of the second sexual stimulation device 500. The modules of the remote interactive control system 40 also can include functionality represented as hardware or integrated circuits, or as software and hardware combinations, such as a special-purpose processor or a general-purpose processor with special-purpose firmware.

In other embodiment, the all of modules of the remote interactive control system 10 can be stored in the first storage unit 130 of the first intelligent terminal 100 and executed by the first processing unit 110 of the first intelligent terminal 100, or can be stored in the second storage unit 230 of the first sexual stimulation device 200 and executed by the second processing unit 210 of the first sexual stimulation device 200, or can be stored in the third storage unit 430 of the second intelligent terminal 400 and executed by the third processing unit 410 of the third intelligent terminal 400, or can be stored in the fourth storage unit 530 of the second sexual stimulation device 500 and executed by the fourth processing unit 510 of the first sexual stimulation device 500, or can be stored in the fifth storage unit 630 of the remote server 600 and executed by the fifth processing unit 610 of the remote server 600.

In one embodiment, the third processing unit 410, the fourth processing unit 510 and the fifth processing unit 610 can be a central processing unit, a digital signal processor, or a single chip, for example. In one embodiment, the third storage unit 430, the fourth storage unit 530 and the fifth storage unit 630 can be an internal storage system, such as a flash memory, a random access memory (RAM) for temporary storage of information, and/or a read-only memory (ROM) for permanent storage of information. The third storage unit 430, the fourth storage unit 530 and the fifth storage unit 630 can also be a storage system, such as a hard disk, a storage card, or a data storage medium. The third storage unit 430, the fourth storage unit 530 and the fifth storage unit 630 can include volatile and/or non-volatile storage devices. In at least one embodiment, the third storage unit 430, the fourth storage unit 530 and the fifth storage unit 630 can include two or more storage devices such that one storage device is a memory and the other storage device is a hard drive. Additionally, the third storage unit 430, the fourth storage unit 530 and the fifth storage unit 630 can be respectively located either entirely or partially external relative to the second intelligent terminal 400, the second sexual stimulation device 500 and the remote server 600.

The first submitting module 12 can be used to control the second communication unit 220 to submit the first detect signal to the first intelligent terminal 100 and the first detect signal can be then relayed to the remote server 600 by the first intelligent terminal 100 or the first submitting module 12 can be further used to control the second communication unit 220 to submit the first detect signal to the remote server 600 directly.

The data exchange control module 41 can be used to relay the first detect signal to the second intelligent terminal 400.

The second display control unit 460 of the second intelligent terminal 400 can be used to control the second display unit 450 to display the detected pressure and the detected speed by dynamic graphics according to the first detect signal and when the detected pressure and the detected speed are displayed by the second display unit 450, the other user can read both the detected pressure and the detected speed, and select a suitable vibration mode and/or a suitable vibration strength according to both the detected pressure and the detected speed.

The second instruction module 42 can be used to generate a second control signal containing a vibration mode and/or a vibration strength in response to the other user's input operation applied on the second input unit 440 and further control the third communication unit 420 to transmit the second control signal to the remote server 600.

The data exchange control module 41 can be further used to relay the second control signal to the first intelligent terminal 100 and the second control signal can be further relayed to the first sexual stimulation device 200 by the first intelligent terminal 100.

The first vibration control module 14 can be further used to control the first vibration unit 240 of the first sexual stimulation device 200 to vibrate according to the second control signal.

The second data obtaining module 43 can be used to obtain the detected pressure and the detected speed detected by the second detection unit 550 and further generate a second detect signal containing the detected pressure and the detected speed.

The second submitting module 44 can be used to control the fourth communication unit 520 of the second sexual stimulation device 500 to submit the second detect signal to the second intelligent terminal 400 and the second detect signal can be relayed to the remote server 600 by the second intelligent terminal 400 or the second submitting module 44 can be further used to control the fourth communication unit 520 to submit the second detect signal to the remote server 600 directly.

The second display control unit 460 of the second intelligent terminal 400 can be used to control the second display unit 450 to display the detected pressure and the detected speed by dynamic graphics according to the second detect signal and when the detected pressure and the detected speed are displayed by the second display unit 450, the other user can read the detected pressure and the detected speed and select a suitable vibration mode and/or a suitable vibration strength according to the detected pressure and the detected speed.

The second instruction module 42 can be used to generate a third control signal containing a vibration mode and/or a vibration strength in response to the other user's input operation applied on the second input unit 440 and further control the third communication unit 420 of the second intelligent terminal 400 to transmit the third control signal to the second sexual stimulation device 500.

The second vibration control module 45 can be used to control the second vibration unit 540 of the second sexual stimulation device 500 to vibrate according to the third control signal.

The data exchange control module 41 can be further used to relay the second detect signal to the first intelligent terminal 100.

The first display control unit 160 of the first intelligent terminal 100 can be further used to control the first display unit 150 to display the detected pressure and the detected speed by dynamic graphics according to the second detect signal and when the detected pressure and the detected speed are displayed by the first display unit 150, the user can read the detected pressure and the detected speed, and select a suitable vibration mode and/or a suitable vibration strength according to both the detected pressure and the detected speed.

The first instruction module 13 can be used to generate a fourth control signal containing a vibration mode and/or a vibration strength in response to the user's input operation applied on the first input unit 140 and further control the first communication unit 120 of the first intelligent terminal 100 to transmit the fourth control signal to the remote server 600.

The data exchange control module 41 can be further used to relay the fourth control signal to the second intelligent terminal 400 and the fourth control signal can be then relayed to the second sexual stimulation device 500.

The second vibration control module 45 can be used to control the second vibration unit 540 of the second sexual stimulation device 500 to vibrate according to the fourth control signal.

The second control signal can contain control information and the control information can be stored in the third storage unit 430 if the user of the first intelligent terminal 100 and the other user of the second intelligent terminal 400 both select to store the control information. In detail, the second storage control module 46 can be used to pop a second dialog box containing a "yes" option and a "no" option to ask the other user whether to store the control information contained in the second control signal in response to the second control signal and the first storage control module 15 can be used to pop a third dialog box containing a "yes" option and a "no" option to ask the user whether to store the control information contained in the second control signal in response to the second control signal and further control the third storage unit 430 to store the control information contained in the second control signal in response to both the user's input operation of selecting the "yes" option applied on the first input unit 140 and the other user's input operation of selecting the "yes" option applied on the second input unit 440.

The third control signal can contain control information and the control information can be stored in the third storage unit 430 if the other user selects to store the control information. In detail, the second storage control module 45 can be further used to pop a fourth dialog box containing a "yes" option and a "no" option to ask the other user whether to store the control information contained in the third control signal in response to the third control signal and further control the third storage unit 130 to store the control information contained in the third control signal in response to the other user's input operation of selecting the "yes" option applied on the second input unit 440 or not to store the control information contained in the third control signal in response to the other user's input operation of selecting the "no" option applied on the second input unit 440.

The fourth control signal can contain control information and the control information can be stored in the first storage unit 130 if both the user and the other user select to store the control information. In detail, the first storage control module 15 can be used to pop a fifth dialog box containing a "yes" option and a "no" option to ask the other user whether to store the control information contained in the fourth signal in response to the fourth control signal and the second storage control module 46 can be used to pop a sixth dialog box containing a "yes" option and a "no" option to ask the other user whether to store the control information contained in the fourth signal in response to the fourth control signal and further control the first storage unit 130 to store the control information contained in the fourth control signal in response to both the user's input operation of selecting the "yes" option applied on the first input unit 140 and the other user's input operation of selecting the "yes" option applied on the second input unit 440.

The remote control method of first sexual stimulation device 200 controlled by a first intelligent terminal 100 is similar to the above control method shown in FIG. 3.

Figure 6:
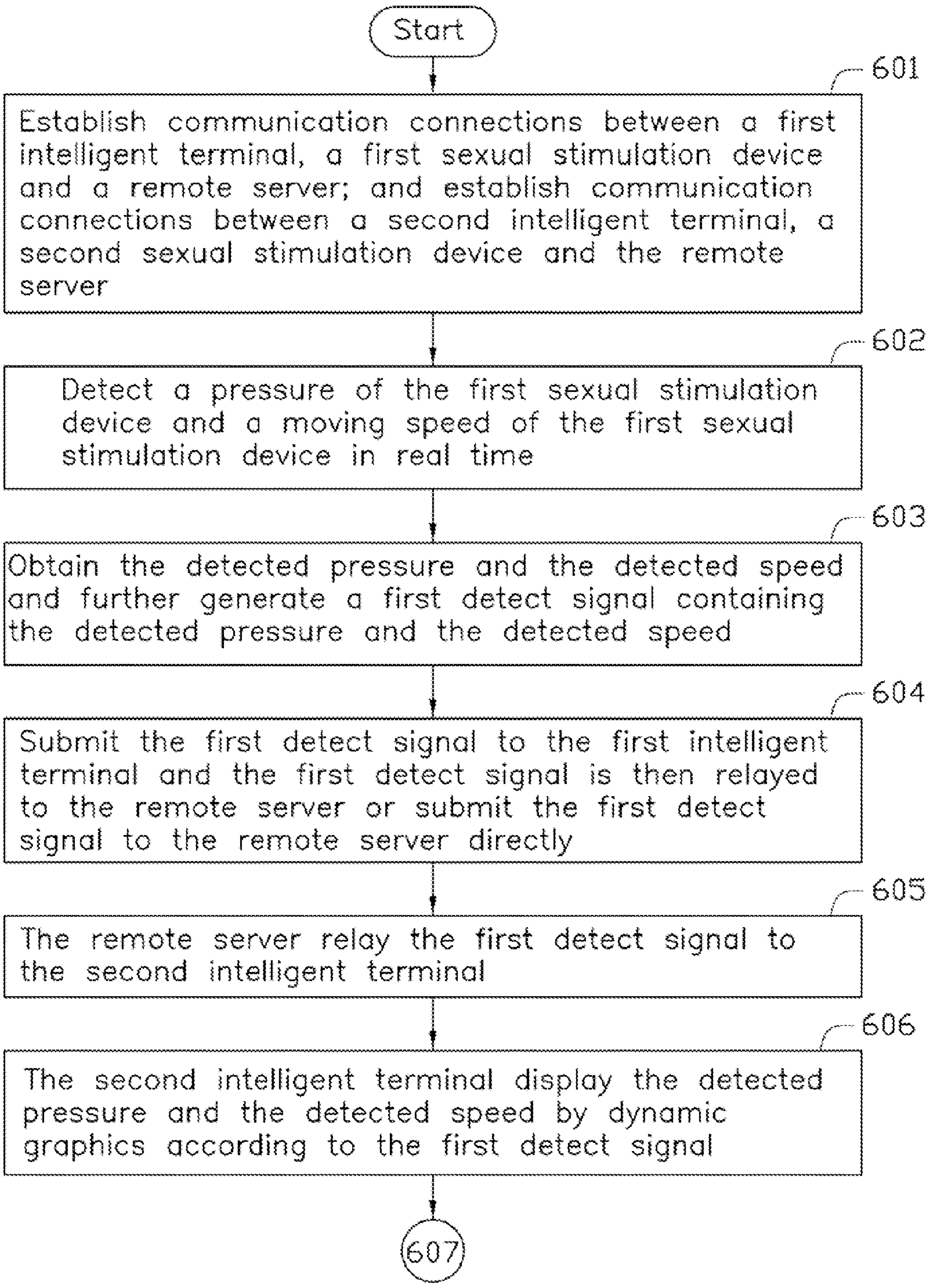
FIGS. 6 and 7 cooperatively show a signal flowchart diagram of an embodiment of a remote interactive control method.
Figure 7:
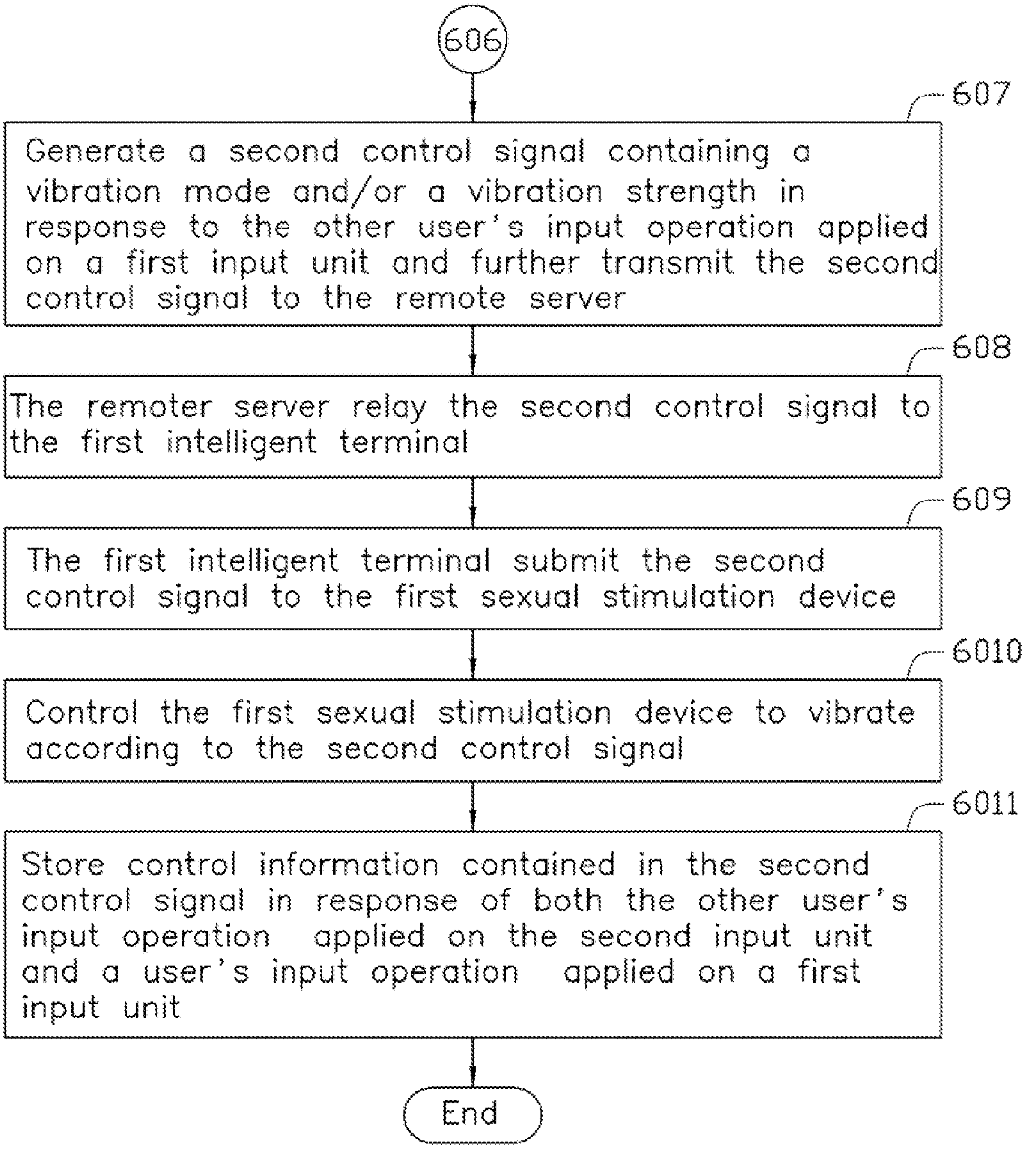

FIGS. 6 and 7 cooperatively illustrate an embodiment of a signal flowchart of a remote control method for a first sexual stimulation device controlled by a second intelligent terminal via a remote server. The method is provided by way of example, as there are a variety of ways to carry out the method. The method described below can be carried out using the configurations illustrated in FIG. 4, for example, and various elements of these figures are referenced in explaining the example method. Each block shown in FIGS. 6 and 7 represents one or more processes, methods, or subroutines carried out in the example method. Additionally, the illustrated order of blocks is by example only and the order of the blocks can be changed. The example method can begin at block 601.

At block 601, a first communication unit of a first intelligent terminal, a second communication unit of the first sexual stimulation device and a fifth communication unit of the remote server establish communication connections between the first intelligent terminal, the first sexual stimulation device and the remote server; a third communication unit of the second intelligent terminal, a fourth communication unit of a second sexual stimulation device and the fifth communication unit of the remote server establish communication connections between the second intelligent terminal, the second sexual stimulation device and the remote server.

At block 602, a first detection unit detects a pressure of the first sexual stimulation device and a moving speed of the first sexual stimulation device in real time.

At block 603, a first data obtaining module obtains the detected pressure and the detected speed and further generates a first detect signal containing the detected pressure and the detected speed.

At block 604, a first submitting module controls the second communication unit of the first sexual stimulation device to submit the first detect signal to the first intelligent terminal and the first detect signal is relayed to the remote server, or the first submitting module controls the second communication unit of the first sexual stimulation device to submit the first detect signal to the remote server directly.

At block 605, a data exchange control module relays the first detect signal to the second intelligent terminal.

At block 606, a second display control unit of the second intelligent terminal controls a second display unit of the second intelligent terminal to display the detected pressure and the detected speed by dynamic graphics according to the first detect signal.

At block 607, a second instruction module generates a second control signal containing a vibration mode and/or a vibration strength in response to the other user's input operation applied on a second input unit and further controls the third communication unit to transmit the second control signal to the remote server.

At block 608, the data exchange control module relays the second control signal to the first intelligent terminal.

At block 609, the first submitting module controls the second communication unit to submit the second control signal to the first sexual stimulation device.

At block 6010, a first vibration control module controls a first vibration unit of the first sexual stimulation device to vibrate according to the second control signal.

At block 6011, a second storage control module controls a third storage unit to store the control information contained in the second control signal in response to both the other user's input operation of selecting a "yes" option applied on the second input unit and a user's input operation of selecting the "yes" option applied on a first input unit.

Figure 8:
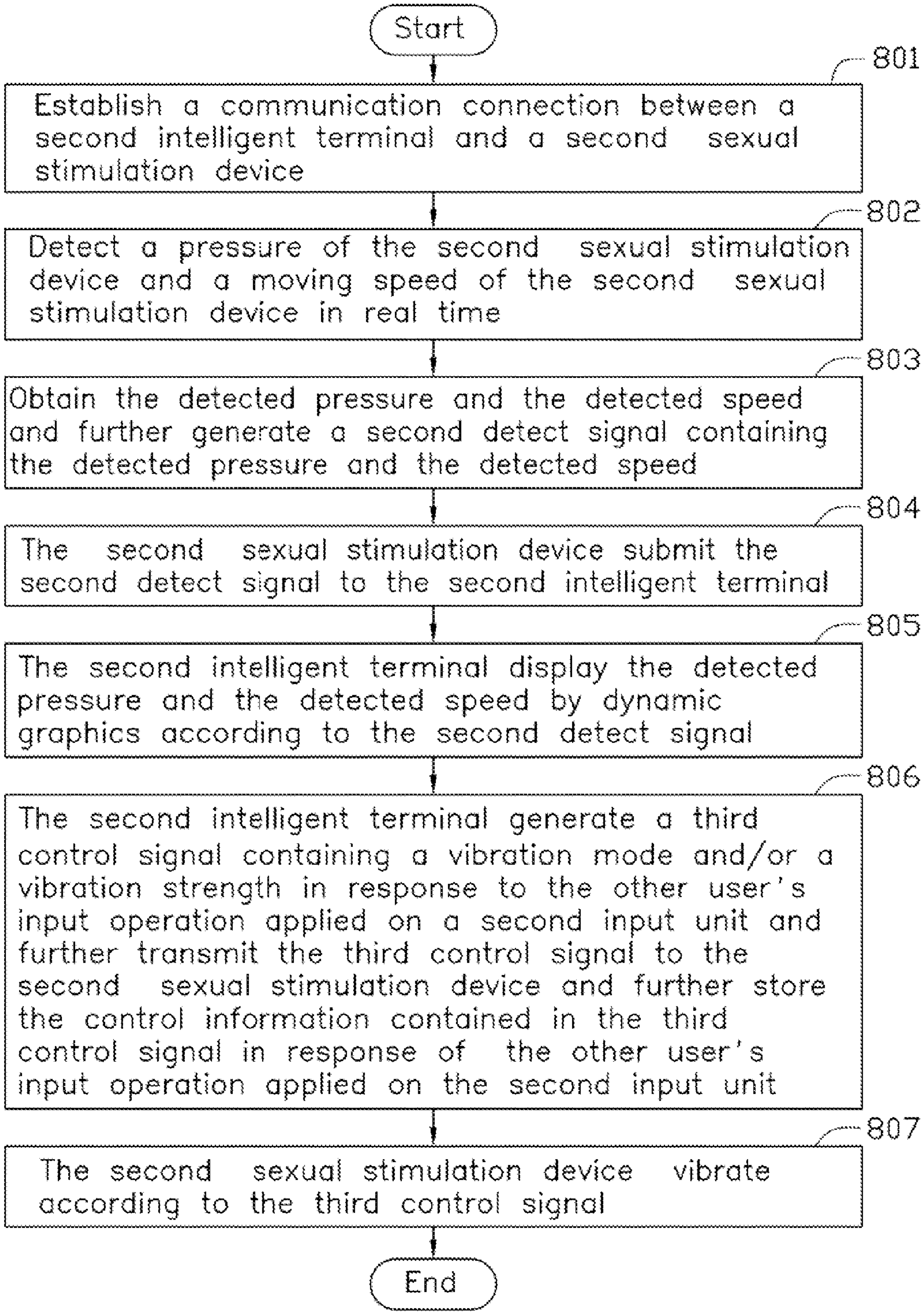
FIG. 8 is a flowchart diagram of an embodiment of a remote interactive control method.

FIG. 8 illustrates an embodiment of a flowchart of a remote control method of second sexual stimulation device 500 controlled by a second intelligent terminal 40. The method is provided by way of example, as there are a variety of ways to carry out the method. The method described below can be carried out using the configurations illustrated in FIG. 4, for example, and various elements of these figures are referenced in explaining the example method. Each block shown in FIG. 8 represents one or more processes, methods, or subroutines carried out in the example method. Additionally, the illustrated order of blocks is by example only and the order of the blocks can be changed. The example method can begin at block 801.

At block 801, a third communication unit of the second intelligent terminal and a fourth communication unit of the second sexual stimulation device establish a communication connection between the second intelligent terminal and the second sexual stimulation device.

At block 802, a second detection unit of the second sexual stimulation device detects a pressure of the second sexual stimulation device and a moving speed of the second sexual stimulation device in real time.

At block 803, a second data obtaining module obtains the detected pressure and the detected speed detected by the second detection unit and further generates a second detect signal containing the detected pressure and the detected speed.

At block 804, a second submitting module controls the fourth communication unit of the second intelligent terminal to submit the second detect signal to the second intelligent terminal.

At block 805, a second display control unit of the second intelligent terminal controls a second display unit of the second intelligent terminal to display the detected pressure and the detected speed by dynamic graphics according to the second detect signal.

At block 806, a second instruction module generates a third control signal containing a vibration mode and/or a vibration strength in response to the other user's input operation applied on the second input unit and further controls the third communication unit of the second intelligent terminal to transmit the third control signal to the second sexual stimulation device and further control the second storage unit of the second intelligent terminal to store the control information contained in the third control signal in response to other user's input operation of selecting a "yes" option applied on a second input unit of the second intelligent terminal.

At block 807, a second vibration control module controls a second vibration unit of the second sexual stimulation device to vibrate according to the third control signal.

Figure 9:
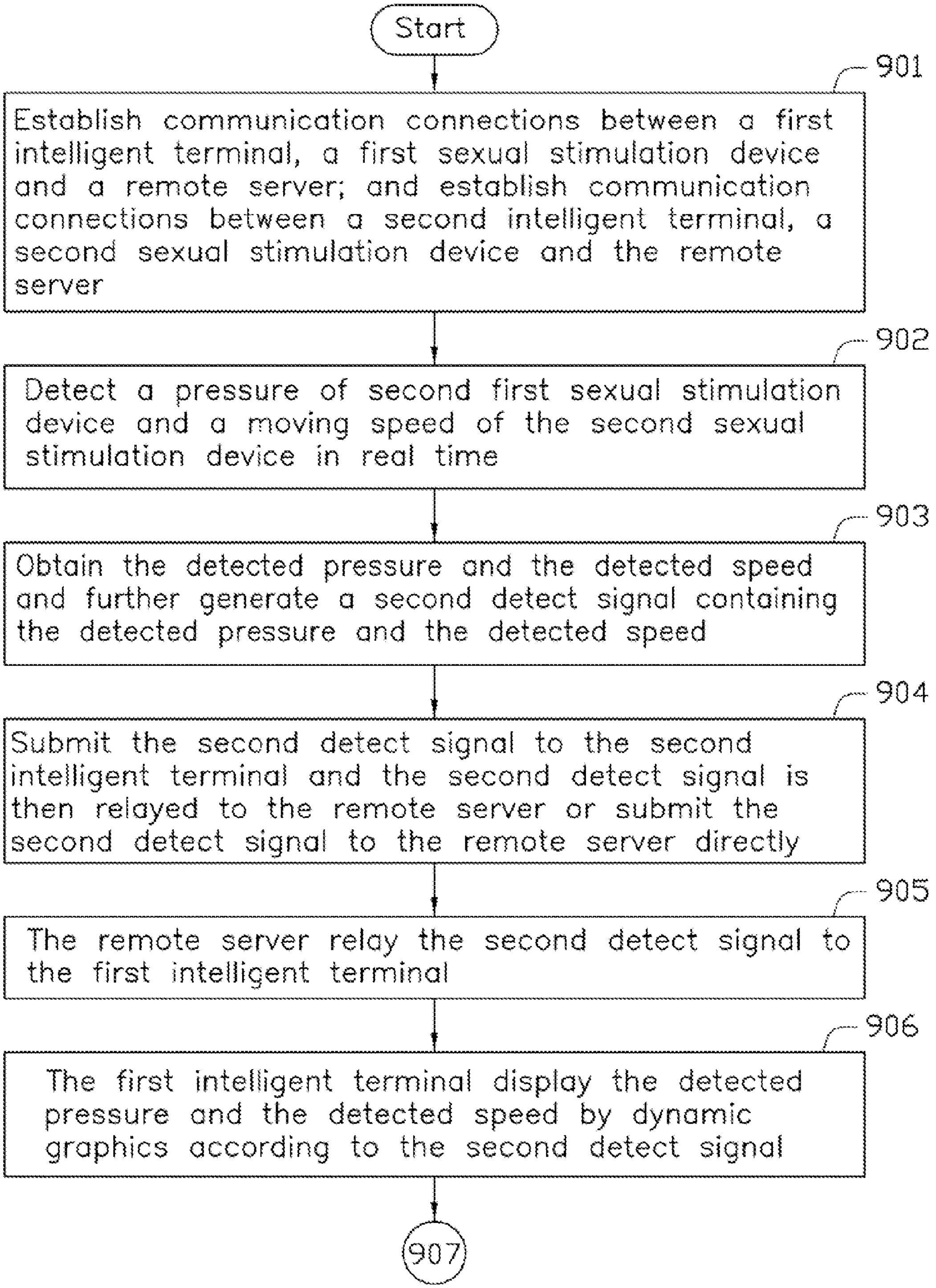
FIGS. 9 and 10 cooperatively show a signal flowchart diagram of other embodiment of a remote interactive control method.
Figure 10:
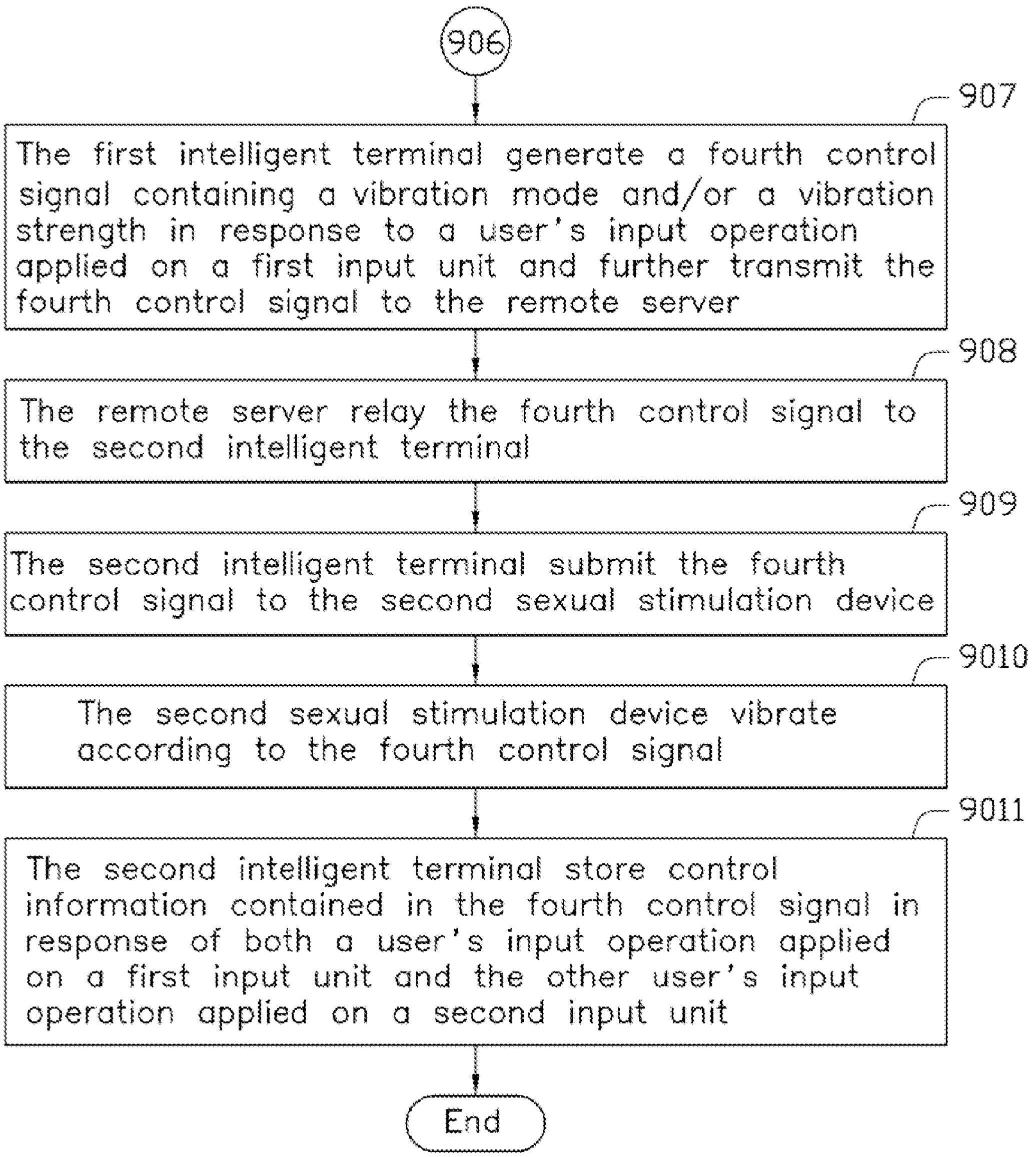

FIGS. 9 and 10 cooperatively illustrate an embodiment of a signal flowchart of the remote control method of a second sexual stimulation device controlled by a first intelligent terminal via a remote server. The method is provided by way of example, as there are a variety of ways to carry out the method. The method described below can be carried out using the configurations illustrated in FIG. 4, for example, and various elements of these figures are referenced in explaining the example method. Each block shown in FIGS. 9 and 10 represents one or more processes, methods, or subroutines carried out in the example method. Additionally, the illustrated order of blocks is by example only and the order of the blocks can be changed. The example method can begin at block 901.

At block 901, a first communication unit of the first intelligent terminal, a second communication unit of a first sexual stimulation device and a fifth communication unit of the remote server establish communication connections between the first intelligent terminal, the first sexual stimulation device and the remote server; a third communication unit of a second intelligent terminal, a fourth communication unit of the second sexual stimulation device and a fifth communication unit of the remote server establish communication connections between the second intelligent terminal, the second sexual stimulation device and the remote server.

At block 902, a second detection unit of the second sexual stimulation device detects a pressure of the second sexual stimulation device and a moving speed of the second sexual stimulation device in real time.

At block 903, a second data obtaining module obtains the detected pressure and the detected speed detected by the second detection unit and further generates a second detect signal containing the detected pressure and the detected speed.

At block 904, a second submitting module controls the fourth communication unit of the second sexual stimulation device to submit the second detect signal to the second intelligent terminal and the second detect signal is relayed to the remote server by the second intelligent terminal; or the second submitting module controls the fourth communication unit to submit the second detect signal to the remote server directly.

At block 905, a data exchange control module relays the second detect signal to the first intelligent terminal.

At block 906, a first display control unit of the first intelligent terminal controls a first display unit of the first intelligent terminal to display the detected pressure and the detected speed by dynamic graphics according to the second detect signal.

At block 907, a first instruction module generates a fourth control signal containing a vibration mode and/or a vibration strength in response to a user's input operation applied on a first input unit and further controls the first communication unit of the first intelligent terminal to transmit the first control signal to the remote server.

At block 908, the data exchange control module relays the fourth control signal to the second intelligent terminal.

At block 909, the second submitting module further controls the fourth communication unit to submit the fourth control signal to the second sexual stimulation device.

At block 9010, a second vibration control module controls a second vibration unit of the second sexual stimulation device to vibrate according to the fourth control signal.

At block 9011, a first storage control module controls a first storage unit to store the control information contained in the fourth control signal in response to both a user's input operation of selecting the "yes" operation applied on the first input unit and the other user's input operation of selecting the "yes" operation applied on a second input unit.

The embodiments shown and described above are only examples. Many details are often found in the art. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A control system, applied to an intelligent terminal and a sexual stimulation device, the intelligent terminal comprising an input unit, a display unit and a display control unit, the sexual stimulation device comprising a vibration unit and a detection unit, the detection unit being used for detecting a pressure of the sexual stimulation device and a moving speed of the sexual stimulation device; the control system comprising a plurality of processing units and a plurality of modules which are collections of instructions executed by the plurality of processing units, the plurality of modules comprising:

a data obtaining module configured to obtain the detected pressure and the detected speed and further generate a detect signal containing the detected pressure and the detected speed;

a submitting module configured to submit the detect signal to the intelligent terminal, and the display control module configured to control the display unit to display the detected pressure and the detected speed by dynamic graphics according to the detect signal;

an instruction module configured to generate a control signal in response to a user's input operation applied on the input unit and further transmit the control signal to the sexual stimulation device; and a vibration control module configured to control the vibration unit to vibrate according to the control signal.

2. The control system of claim 1, wherein the intelligent terminal comprises a first storage unit, the sexual stimulation device comprises a second storage unit, the first storage unit and the second storage unit both store a number of vibration modes and a number of vibration strength, the control signal is generated by selecting a vibration mode and a vibration strength from the first storage unit, and the vibration control module configured to control the vibration unit to vibrate according to the selected vibration mode and the selected vibration strength in response to the control signal.

3. The control system of claim 2, the plurality of modules comprising:

a storage control module configured to store the selected vibration mode and the selected vibration strength contained in the first control signal.

4. A control method, applied to a sexual stimulation device comprising a vibration unit, the control method comprising:

establishing a communication connection between the sexual stimulation device and an intelligent terminal;

detecting a pressure of the sexual stimulation device and a moving speed of the sexual stimulation device in real time;

obtaining the detected pressure and the detected speed and further generating a detect signal containing the detected pressure and the detected speed;

submitting the detect signal to the intelligent terminal and the intelligent terminal generating a control signal according to the detect signal;

receiving the control signal transmitted by the intelligent terminal; and controlling the sexual stimulation device to vibrate according to the control signal.

5. The remote method of claim 4, wherein the control method further comprising:

storing control information contained in the first control signal.

6. The remote method of claim 5, wherein the control method further comprising:

detecting a pressure of the sexual stimulation device and a moving speed of the sexual stimulation device in real time for monitoring while the vibration device is vibrating.

7. A remote interactive control system, applied to at least one first intelligent terminal, at least one first sexual stimulation device wirelessly connected to the at least one first intelligent terminal, at least one second intelligent terminal, at least one second sexual stimulation device wirelessly connected to the at least one second intelligent terminal and a remote server; the first intelligent terminal comprising a first input unit, the first sexual stimulation device comprising a first vibration unit and a first detection unit, the first detection unit being used for detecting a pressure of the first sexual stimulation device or a moving speed of the first sexual stimulation device; the second intelligent terminal comprising a second input unit; the second sexual stimulation device comprising a second vibration unit and a second detection unit, the second detection unit being used for detecting a pressure of the second sexual stimulation device or a moving speed of the second sexual stimulation device; the remote interactive control system comprising a plurality of processing units and a plurality of modules which are collections of instructions executed by the plurality of processing units, the plurality of modules comprising:

a first data obtaining module configured to obtain the detected pressure and the detected speed of the first sexual stimulation device and further generate a first detect signal containing the detected pressure and the detected speed;

a first submitting module configured to submit the first detect signal to the remote server;

a data exchange control module configured to relay the first detect signal to the second intelligent terminal;

a second instruction module configured to generate a first control signal in response to a user's input operation applied on the second input unit and further transmit the first control signal to the remote server;

the data exchange control module further configured to relay the first control signal to the first intelligent terminal and the first control signal further being relayed to the first sexual stimulation device by the first intelligent terminal; and a first vibration control module configured to control the first vibration unit of the first sexual stimulation device to vibrate according to the first control signal.

8. The remote interactive control system of claim 7, the plurality of modules comprising:

a first instruction module configured to generate a second control signal in response to other user's input operation applied on the first input unit and further transmit the second control signal to the first sexual stimulation device; the first vibration control module is further configured to control the first vibration unit of the first sexual stimulation device to vibrate according to the second control signal.

9. The remote interactive control system of claim 7, the plurality of modules comprising:

a second data obtaining module configured to obtain the detected pressure and the detected speed of the second sexual stimulation device and further generate a second detect signal containing the detected pressure and the detected speed;

a second submitting module configured to submit the second detect signal to the second intelligent terminal;

a second instruction module configured to generate a third control signal in response to the other user's input operation applied on the second input unit and further transmit the third control signal to the second sexual stimulation device; and a second vibration control module configured to control the second vibration unit of the second sexual stimulation device to vibrate according to the third control signal.

10. The remote interactive control system of claim 9, wherein the second detect signal is relayed to the remote server by the second intelligent terminal and the second submitting module is configured to submit the second detect signal to the remote server;

the data exchange control module is further configured to relay the second detect signal to the first intelligent terminal;

the first instruction module is further configured to generate a fourth control signal and further transmit the first control signal to the remote server;

the data exchange control module is further configured to relay the fourth control signal to the second intelligent terminal;

the second submitting module is further configured to submit the fourth control signal to the second sexual stimulation device; and the second vibration control module is further configured to control the second vibration unit of the second sexual stimulation device to vibrate according to the fourth control signal.

11. The remote interactive control system of claim 10, the plurality of modules comprising:

a first storage control module configured to control the first intelligent terminal to store control information contained in the second control signal and the fourth control signal.

12. The remote interactive control system of claim 10, the plurality of modules comprising:

a second storage control module configured to control the second intelligent terminal to store control information contained in the first control signal and the third control signal.

13. The remote interactive control system of claim 7, wherein the detected pressure and the detected speed are displayed by the first intelligent terminal or the second intelligent terminal in dynamic graphics.

14. A remote interactive control method, applied to at least one first intelligent terminal, at least one first sexual stimulation device wirelessly connected to the at least one first intelligent terminal, at least one second intelligent terminal, at least one second sexual stimulation device wirelessly connected to the at least one second intelligent terminal and a remote server; the first sexual stimulation device comprising a first vibration unit; the second sexual stimulation device comprising a second vibration unit; the remote interactive control method comprising a plurality of steps, the steps comprising:

the first sexual stimulation device detecting a pressure of the first sexual stimulation device or a moving speed of the first sexual stimulation device the first sexual stimulation device obtaining the detected pressure and the detected speed of the first sexual stimulation device and further generating a first detect signal containing the detected pressure and the detected speed;

the first sexual stimulation device submitting the first detect signal to the remote server;

the remote server relaying the first detect signal to the second intelligent terminal;

the second intelligent terminal generating a first control signal and further transmitting the first control signal to the remote server;

the remote server relaying the first control signal to the first intelligent terminal and the first intelligent terminal relaying the first control signal to the first sexual stimulation device; and the first sexual stimulation device controlling the first vibration unit of the first sexual stimulation device to vibrate according to the first control signal.

15. The remote interactive control method of claim 14, the steps further comprising:

the first sexual stimulation device generating a second control signal according to the first detect signal and further transmitting the first control signal to the first sexual stimulation device; and the first sexual stimulation device controlling the first vibration unit of the first sexual stimulation device to vibrate according to the second control signal.

16. The remote interactive control method of claim 14, the steps further comprising:

the second sexual stimulation device detecting a pressure thereof or a moving speed thereof;

the second sexual stimulation device obtaining the detected pressure and the detected speed and further generate a second detect signal containing the detected pressure and the detected speed;

the second sexual stimulation device submitting the second detect signal to the second intelligent terminal;

the second intelligent terminal generating a third control signal and transmitting the third control signal to the second sexual stimulation device; and the second sexual stimulation device controlling the second vibration unit of the second sexual stimulation device to vibrate according to the third control signal.

17. The remote interactive control method of claim 16, the steps further comprising:

the second intelligent terminal relaying the second detect signal to the remote server or the second sexual stimulation device submitting the second detect signal to the remote server;

the remote server relaying the second detect signal to the first intelligent terminal;

the first intelligent terminal generating a fourth control signal and further transmitting the first control signal to the remote server;

the remote server relaying the fourth control signal to the second intelligent terminal and then submitting the fourth control signal to the second sexual stimulation device; and the second sexual stimulation device controlling the second vibration unit of the second sexual stimulation device to vibrate according to the fourth control signal.

18. The remote interactive control method of claim 17, the steps further comprising: store control information contained in the first control signal and the third control signal.

19. The remote interactive control method of claim 17, the steps further comprising: store control information contained in the second control signal and the fourth control signal.

20. The remote interactive control method of claim 16, the steps further comprising: displaying the detected pressure and the detected speed in dynamic graphics.

* * * * *